United States Patent
Anderson et al.

[11] Patent Number: 5,815,242
[45] Date of Patent: Sep. 29, 1998

[54] WIDE FIELD SCANNING LASER OPTHALMOSCOPE

[75] Inventors: Douglas Crombie Anderson, Dollar; Roger Albert Lucas, Kirkcaldy; Robert Henderson, Edinburgh, all of Great Britain

[73] Assignee: OPTOS Public Limited Company, Fife, United Kingdom

[21] Appl. No.: 640,913

[22] PCT Filed: Nov. 9, 1994

[86] PCT No.: PCT/GB94/02465

§ 371 Date: May 9, 1996

§ 102(e) Date: May 9, 1996

[87] PCT Pub. No.: WO95/13012

PCT Pub. Date: May 18, 1995

[30] Foreign Application Priority Data

Nov. 9, 1993 [GB] United Kingdom ............ 9323065

[51] Int. Cl.⁶ .................................................. A61B 3/10
[52] U.S. Cl. ........................ 351/221; 351/205; 351/246
[58] Field of Search .................................. 351/221, 211, 351/205, 206, 200, 246

[56] References Cited

U.S. PATENT DOCUMENTS

| | | |
|---|---|---|
| 4,213,678 | 7/1980 | Pomerantzeff et al. . |
| 4,755,044 | 7/1988 | Thorn . |
| 4,764,005 | 8/1988 | Webb et al. . |
| 4,765,730 | 8/1988 | Webb . |
| 4,768,873 | 9/1988 | Webb et al. . |
| 4,768,874 | 9/1988 | Webb et al. . |
| 4,893,920 | 1/1990 | Webb . |
| 5,198,845 | 3/1993 | Triller . |
| 5,233,454 | 8/1993 | Sakuma et al. . |
| 5,268,711 | 12/1993 | Poxleitner et al. . |

FOREIGN PATENT DOCUMENTS

| | | |
|---|---|---|
| 0223356 | 5/1987 | European Pat. Off. . |
| 0412667 | 2/1991 | European Pat. Off. . |
| 0495469 | 7/1992 | European Pat. Off. . |
| 2132852 | 11/1984 | United Kingdom . |
| 9000026 | 11/1990 | WIPO . |

*Primary Examiner*—Hung X. Dang
*Attorney, Agent, or Firm*—Ratner & Prestia

[57] ABSTRACT

A scanning ophthalmoscope which produces images of the rear surface of the human eye, and particularly of the retina, by utilising an aspherical mirror to reflect light beams, produced by multiple scanning laser light sources, into the retina. This ophthalmoscope incorporates dynamic systems for the compensation of focus and residual astigmatisms in addition to providing accurate wide field images with adequate resolution and contrast which can be displayed and stored in standard computer systems.

6 Claims, 3 Drawing Sheets

WIDE FIELD SCANNING LASER OPTHALMOSCOPE

The invention relates to a scanning ophthalmoscope for scanning the retina of the eye.

The need for a wide field retinal imaging ophthalmoscope is based on the fact that current fundus camera designs can produce high quality film based images in colour, but are limited in their field of view of the object plane to a maximum of 60 degrees from the pupillary point. Many manufacturers in fact produce less than the 60 degree field of view. Scanning laser ophthalmoscopes currently produce a 40degree field of view in true monochrome or synthesised (not true) colour images. The resolution of the scanned laser-based images may be two to three orders of magnitude less than the film based images, but the advantage of the scanning laser ophthalmoscope is that dynamic images are available for display on standard television monitors. These images may be recorded on standard video tape.

The field of view of both film based cameras and scanning laser ophthalmoscopes may be artificially increased by rotating the camera about a specific centre of rotation, lying between the rear surface of the cornea and the front surface of the lens, the so-called "pupillary point". However, an instrument which produces complete wide field images in one scan, without mechanical machine movement, is valuable in producing more efficient diagnostic information for the clinician. High resolution of the scanning laser ophthalmoscope image enhances interpretation of fine detail, while the production of the image in colour in such an instrument would assist in the clinical diagnostic process particularly for certain diseases such as proliferative diabetic retinopathy.

A limitation exists with the optics of the human eye in that the resolution of an incident-laser beam at the retina is restricted by diffraction to about 10 mms in diameter. This is due to the cornea, lens, and the aqueous and vitreous humours of optical path of the eye. Thus, no image may contain higher resolution than this however the image is produced.

It is the objective of this invention to produce high resolution true colour images in a single scan.

Colour imaging from scanning laser based instruments has been proposed from a variety of sources, but none of these embraces a wide field of view at the retina, in colour and at acceptably high resolution. In order to achieve this, the characteristics of the structure of the optical system of the eye must be examined in more detail than has been carried out to date.

PRIOR ART

In this field it is already known that three generic types of scanning laser ophthalmoscope exist for use in clinical environments. The function and use of the three types are fundamentally different.

The three types may be classified by the manufacturers' names viz;
(1) Rodenstock
(2) Zeiss
(3) Heidelburg The functions of the three types are summarised as follows:

Rodenstock

This system scans the retina of the eye through the use of a tilted spherical mirror. X and Y scans are produced by means of a high speed rotating polygon, and an oscillating galvanometer mirror. Laser beams of wave lengths corresponding to Argon ion (488 nm), Helium Neon (566 nm) and Infra-red (790 nm) are focused through a manually variable focusing system to produce a best image. The scanning system produces pixel image data, by means of an electronic detector system, synchronised with the scanning mirrors to produce data at video rate output. The signal is electronically processed (not through a framestore) to produce an image which is capable of being displayed on an ordinary television monitor. They system is therefore capable of real time dynamic imaging.

The deficiencies of this system are that the image is currently only obtainable in monochrome and has a maximum resolution of approximately 400,000 pixels. The field of view is also restricted to about 32 degrees maximum at this resolution. The mirror system is acknowledged to contain abberations, but no corrections are effected on the instruments, although some cross-scan errors are highlighted for correction through the use of toroidal lenses in later patents.

Heidelburg

The Heidelburg Scanning Laser Tomograph is a laser based scanning design, specifically utilised for examination of the optic disc. The machine is used clinically to diagnose and assess the progress of the disease glaucoma.

The instrument delivers laser light through a fibre optic light guide to the X and Y scanning units which are high speed opto-acoustic deflectors. The field of scan is limited to about 5 degrees, centred on the optic disc, and the scan angle is limited by the pupil of the eye since the centre of scan rotation is external to the eye, and not centred on the pupillary point. The instrument is incapable of wide field retinal imaging in a single scan.

The instrument produces a colour display of the topography of the optic disc. The colours, however, represent differing height levels rather than tissue colour, and so this display is a synthesised image and not a true colour rendition. A flat surface is therefore only imaged as a single colour plane.

The instrument is therefore not a true retinal imaging instrument, and is unable to produce wide field retinal images in representative tissue colour. The prime function of this instrument is to produce topographic representations of the retina.

Zeiss

The Zeiss system is a semi-hybrid version of the Rodenstock and Heidelburg instruments. A spherical mirror is used to increase the scan angle of the instrument by utilising the pupillary point, and the X and Y scans are performed by rotating polygon and galvanometer driven mirrors respectively. The Zeiss utilises fibre-optic incident laser light delivery and returned light conduits to connect to the main instrument processing body. The Zeiss contains only manually controlled patient optics compensation, and also, as for both the Rodenstock and Heidelburg designs, utilises a confocal imaging system to reject unwanted data from the required data returned signal. The use of a confocal detection system enhances the quality of the returned data, rejecting spurious information.

Confocal imaging is utilised in many areas of microscopy, and is a feature of all the instruments detailed above.

SUMMARY OF THE INVENTION

The design set out here defines the implementation of a wide field retinal scanning ophthalmoscope with colour imaging capability that seeks to improve on or eliminate deficiencies of the current designs of scanning laser ophthalmoscopes. To achieve this, it is necessary to look at the implementation of a design which not only has novelty from both electro-optic and mechanical viewpoints, but also addresses the question of the fundamental limitations and imaging qualities of the eye at the extremes of the field of view. No current scanning laser ophthalmoscope is capable of producing images at the extremes of the field of view due to the generalised nature of existing designs for imaging on the central axis of the eye.

According to a first aspect of the present invention there is provided a scanning ophthalmoscope for scanning the retina of an eye, having a laser light source and an aspherical mirror in the path of the light from the light source wherein the light is reflected from the aspherical mirror for incidence with the retina of the eye.

Preferably, the aspherical mirror is ellipsoidal.

Preferably, the ophthalmoscope includes a means for producing a two dimensional scan.

The means for producing a two dimensional scan may include a rotating mechanism and an oscillating mechanism.

Preferably, the rotating mechanism is a rotating polygon reflector scanner and the oscillating mechanism is a galvanometer scanner.

The means for producing a two dimensional scan act with a non-transmissive scanning compensator to provide a virtual point which is coincident with one focus of the ellipsoidal mirror.

The non-transmissive scanning compensator may be a scanning prism. Alternatively, it may be an arrangement of an off-axis aspheric mirror and a galvanometer or a rotating polygon.

The rotating polygon reflector scanner may be positioned prior to the galvanometer scanner in the path of the incident beam from the light source.

Preferably, the ellipsoidal mirror is orientated such that the sagittal focus is shorter than the tangential focus, ie the sagittal focus point is in front of the tangential focus point.

Preferably, the ophthalmoscope includes an active control mechanism to vary astigmatism compensation during a retinal scan cycle. The astigmatism compensation may be varied in accordance with the data of a return beam after incidence with the retina.

Preferably, compensation means are provided in the form of an assembly of short focal length optics which compensation means are adjusted in relation to the active control mechanism.

Preferably, the compensation means are arranged to act on the incident and return beams.

Preferably, the ophthalmoscope includes a focus compensation which is active during a scan of the retina which focus compensation compensates for distorted retinal surfaces and/or the refractive nature of the eye.

Preferably, the laser light source is a semi conductor diode laser.

Preferably, there are a plurality of laser light sources.

Preferably, the ellipsoidal mirror is either a front surface mirror or a combined reflective/refractive mirror.

According to a second aspect of the present invention there is provided a scanning ophthalmoscope for scanning the retina of an eye, having a laser light source, a means for producing a two-dimensional scan and a non-transmissive scanning compensator disposed to intersect the incident light before reaching the retina wherein the non-transmissive scanning compensator provides a virtual point from which the beam scan of the retina appears to originate.

Preferably, the non-transmissive scanning compensator is a scanning prism.

Preferably, the means for producing an area scan includes a galvanometer scanner and a rotating polygon reflector scanner.

The galvanometer scanner may be before or after the rotating polygon reflector scanner in the incident beam of the laser light source.

Preferably, the retinal scanning ophthalmoscope includes an aspherical mirror.

Preferably, the galvanometer scanner is the final scanner before the incidence beam reaches the aspherical mirror.

The aspherical mirror may be in the form of an ellipsoidal mirror and the virtual point may be coincident with one focus of the ellipsoidal mirror.

Preferably, the scanning prism compensates for a lateral shift to the incidence and output beams.

Preferably, the ophthalmoscope of the second aspect has some or all of the features of the ophthalmoscope of the first aspect of the present invention.

According to a third aspect of the present invention there is provided a scanning ophthalmoscope for scanning the retina of an eye, having a laser light source comprising a plurality of laser beams of varying wavelengths in the visible spectrum.

Preferably, the plurality of laser beams are three laser beams of red, green and blue visible wavelengths.

Preferably, the three laser beams have wavelengths of 566 nm, 633 nm and 488 nm.

Preferably, the ophthalmoscope of the third aspect has some or all of the features of the first and/or second aspects of the present invention.

Preferably, output beams of the plurality of laser beams are modulated to produce a retinal image in colour and to produce a patient image target.

Detection of the modulated beams may be sequential of simultaneous.

Preferably, control means are provided to enable positioning of an image target over the retinal image to allow determination of defects in the retina.

According to a fourth aspect of the present invention there is provided a method of scanning a retina of an eye comprising directing a laser light onto a retina via an aspherical mirror.

Preferably, means are provided for producing an area scan of the retina.

According to a fifth aspect of the present invention there is provided a method of scanning a retina of an eye comprising directing laser light onto a retina in the form of an area scan wherein a galvanometer scanner is used for the area scan and a scanning prism intersects the light and provides a virtual point.

BRIEF DESCRIPTION OF THE DRAWINGS

Embodiments of the present invention will now be described with reference to the accompanying drawings in which.

DESCRIPTION OF THE PREFERRED EMBODIMENTS

Figure 2:
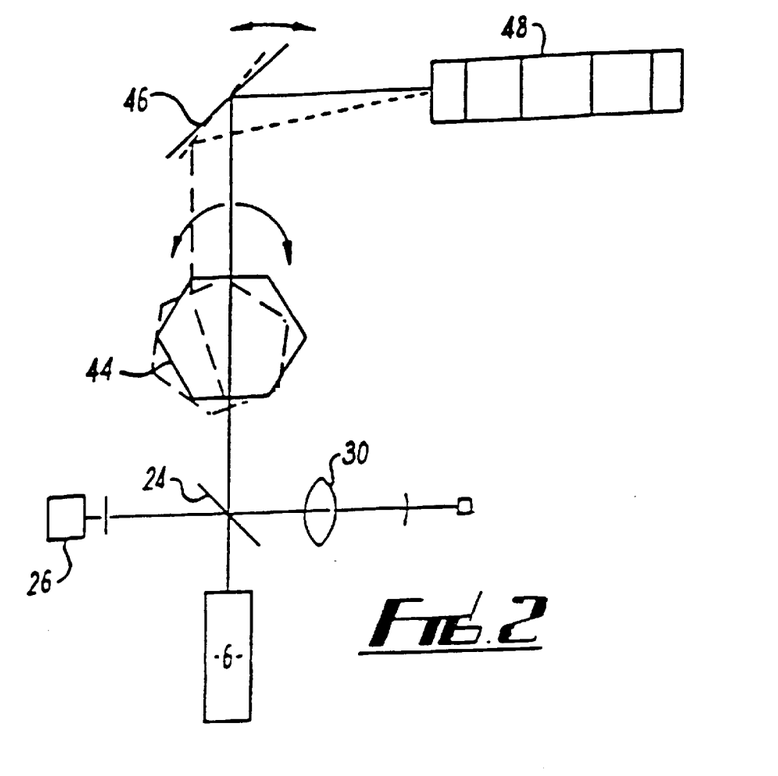
FIG. 2 is a detail of the scanning ophthalmoscope of FIG. 1.
Figure 3:
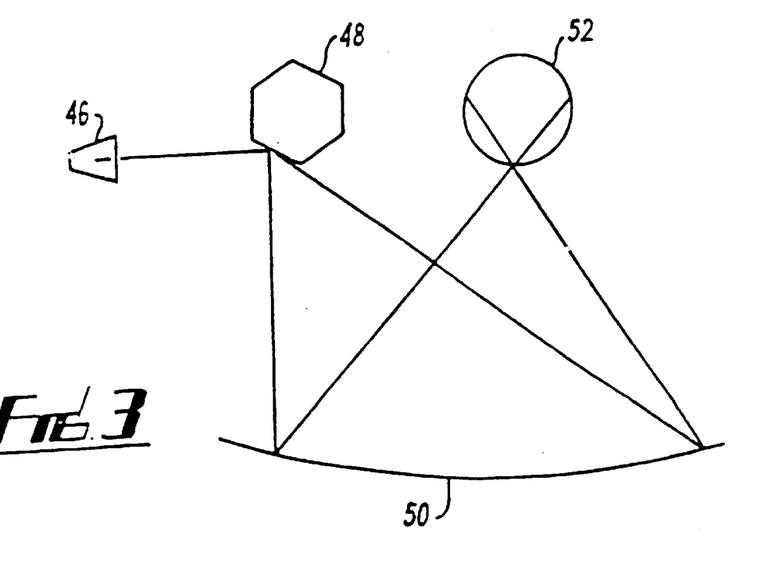
FIG. 3 is a simplified detail of the scanning ophthalmoscope of FIG. 1.
Figure 4:
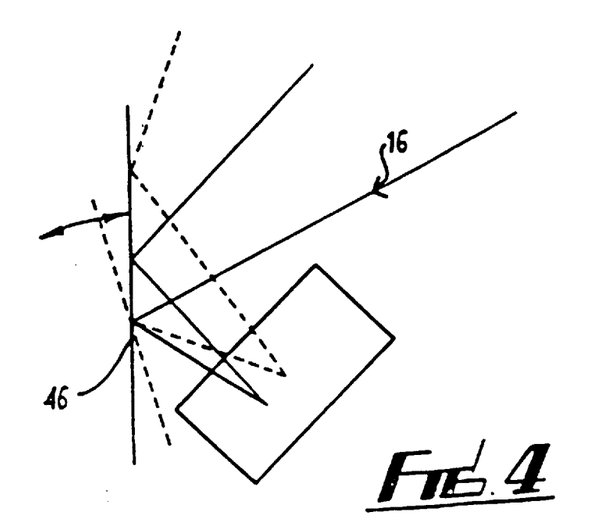
FIG. 4 is a diagram showing a possible scan amplification at the galvanometer scanner of a scanning ophthalmoscope in accordance with the present invention.
Figure 5:
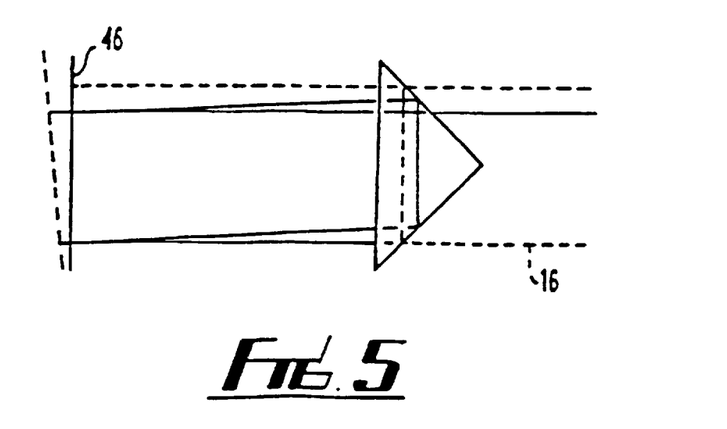
FIG. 5 is a diagram showing a means of compensation for galvanometer tilt errors in a scanning ophthalmoscope in accordance with the present invention.

Referring to the drawings an implementation of the laser scanning ophthalmoscope 2 is described. A scanning ophthalmoscope 2 is used for the production of images of the rear surface of the human eye and specifically of the retina, using a method of scanning multiple laser beams with and through optical systems, utilising scanners, mirrors and optical components to produce digitised (pixelated) images which maybe displayed and stored in industry standard computer systems. The inventions and improvements claimed in this implementation relate to improvements in scanning and imaging technologies to compensate for both eye and machine optical errors and aberrations. Substantial improvements to proprietary scanning methods for the production of accurate pixelated images with adequate resolution and contrast are detailed (FIGS. 2 and 3), as is the incorporation of dynamic (active feedback) systems for the compensation of spherical focus and residual astigmatisms. A method of compensating for errors in the scanners is outlined (FIG. 4) as is a method of increasing beam scan angles by optical means (FIG. 5) rather than mechanical means.

A method of producing digital colour images is detailed, and the essential invention and improvements over existing scanning laser ophthalmoscopes in terms of high field angles (wide field of view at the retina) relating to image resolution is characterised.

An infra-red camera system for operator guidance with no adverse patient impact is described, and the use of infra-red imaging for ophthalmoscope positioning, with a secondary function of eye movement detection is also included. The use of infra-red light has no adverse effect on the pupil response of the eye.

A patient target system is proposed. This will assist the patient with the positioning of the eye, and will also allow the clinical specialist to predict the area of the eye which is actually imaging for the patient. This function is particularly useful when determining ophthalmic errors in young patients.

Figure 1:
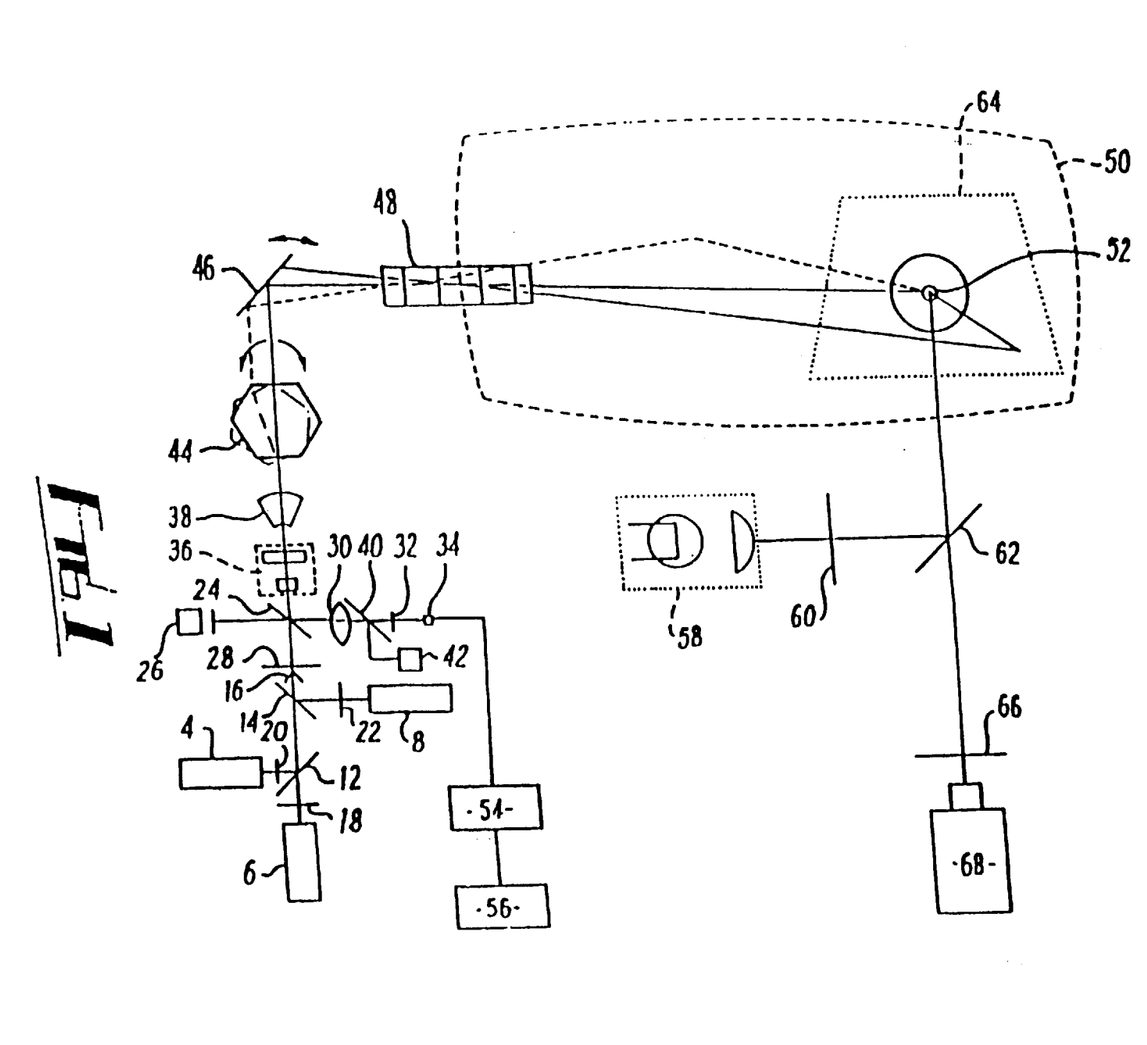
FIG. 1 is an optical schematic of a laser scanning ophthalmoscope according to the present invention indicating the incident path from the laser light source to the eye and from the eye to the detecting element and in which eye positioning elements are also described.

Coherent laser light at selected wavelengths is produced and directed from a first 4, second 6 and third 8 laser source into a common incident beam 16 through a first 12 and second 14 dichroic beam splitter. The coherent laser sources 4,6,8 are so selected that incident beam 16 which exits the second dichroic beam splitter 14 is essentially 'white' light at low powers. Means of colour balancing the lasers from laser sources 4,6,8 for optimum imaging is achieved through first 18, second 20 and third 22 power control filters. A third dichroic beamsplitter 24 has two functions. The first function is that the incident light a proportion of the energy is split off into a power monitor 26 which utilises a photo detector which has suitable filters to monitor the individual lasers from laser sources 4,6,8. The outputs of these detectors is monitored electronically, provides safe level operation and, in the case of malfunction, would cause machine shut down by means of an electrically operated safety shutter 28.

The second function of the third dichroic beamsplitter 24 is to separate the energy returned from the eye by the scanners, and pass this to a focusing lens 30, a confocal aperture 32 (of variable aperture diameter and variable spacing from the detector) and a multiplicity of filters and detectors 34 to produce electronic signal outputs for the returned colour signal levels simultaneously.

Alternatively, a single detector may be used and each colour scanned sequentially, rather than simultaneously, at a loss of image data capture speed.

The collimated beams pass to first 36 and second 38 dynamic compensation elements. The first dynamic compensation element 36 controls the off-axis astigmatism of the eye and the second dynamic compensation element 38 controls the focus during the scan of the retina.

These dynamic compensation elements 36,38 are beam shaping lens assemblies of short focal length optics controlled by piezo actuators, which allow high speed compensation drive motions to be imported to the optics assemblies. Offsets to both the focus and astigmatic correction assemblies can be applied manually for individual patient correction. Dynamic control will utilise feedback in terms of the retinal spot size, which will be detected at a defocus position of the returned image point which will be detected by a fourth dichroic beam splitter 40 and an array detector 42.

The incident beam 16 is then directed to a scanning transmissive prism 44 whose functions is to eliminate cross-scan error at the scan, or pupillary, point of the eye. The scanning prism 44 acts to give lateral shift to the incident beam 16 before further directing said beam on to the reflecting surface of a galvanometer scanner 46. Use of this scanning prism 44 means that the incident beam 16 presents at the surface of the rotating polygon 48 as a virtual point source. The galvanometer scanner 46 provides a vertical scanning motion of the incident beam 16. The speed of this galvanometer 46 determines the frame rate.

From this scanner 46, the incident beam 16 is directed onto a rotating polygon reflector scanner 48 which provides a horizontal scanning motion of the incident beam 16. The relative positions of the galvanometer scanner 46 and the polygonal scanner 48 in the path of the incident beam 16 are the reverse of their relative positions described in known prior art. This arrangement allows the rotating polygon reflector scanner 48 to deliver a two dimensional angular scan from an apparent or virtual point source.

An implementation may be made where the relative positions of the galvanometer scanner 46 and polygon scanner 48 are reversed.

An alternative arrangement is possible for the transmissive scanning prism 44. A galvanometer or rotating polygon may be used in conjunction with an off-axis aspheric reflective surface mirror, or such a form that a scanned angular incident or input beam is reflected by the mirror such that all beams returned from the mirror are parallel for all angles of input beam from the scanning point. Such a form of mirror could be an off-axis paraboloid. This implementation would form the basis of a none transmissive virtual point scanning system for a one dimensional scanner. For a two dimensional scanner, other aspheric forms could be used for scanning. The replacement of a scanning prism requires the addition of both a mirror and a scanning galvanometer or rotating prism, in addition to the galvanometer and rotating polygon for the two dimensional scan of the scanning laser ophthalmoscope.

The incident beam 16 is then directed onto an aspheric mirror 50 which is used to direct and shape the scanning beam at the pupillary point of the eye 52 of the subject. The incident beam enters the eye 52 through the pupil.

The reflected beam, which may have a diameter 5–10 times that of the incident beam 16, is initially directed back along the optical path common with that of the incident beam 16. This reflected beam is collected by the aspheric or ellipsoidal mirror 50 which directs it via the rotating polygon detector scanner 48 and the galvanometer scanner 46 to the scanning prism 44. In this direction, the scanning prism 44 acts to compensate for the lateral shift of the reflected beam before the reflected beam reaches the dynamic focus compensation elements 36,38. This compensation de-scans the return beam, and ensures the return beam is co-incident with the incident beam 16 at the third dichroic beamsplitter 24 thus optimising the data signal of the reflected beam before it is registered by the image data detector 22 at the confocal aperture 32, scanned, used to produce a retinal image and then stored in data arrays for further processing.

In this context the confocal aperture 32 is confocal with the retinal plane under examination, and seeks to eliminate spurious returned data from the retina, and therefore allows only the scanned pixel under consideration to be imaged, so improving contrast of adjacent pixels.

In use, therefore the laser can be any laser light source which provides emission at suitable frequencies. Employment of single wavelength laser illumination produces monochromatic images. However, the production of colour images may be synthesised by scanning using multiple laser beams of varying wavelengths covering the visible spectrum and utilising wavelengths approximating to the three primary colours of light; red, green and blue. The specific wavelengths in the red, green and blue bands 566 mm, 633 mm and 488 mm will give composite colour images. The low average power of illumination required for the laser scan of the retina in a patient means that laser wavelengths in the visible regions are acceptable without undue patient discomfort even without the use of topical mydriasis, (eye pupil dilation), and may be combined into a 'white light' beam for fast scanning.

The laser (coherent) light production may be by several means. Gas lasers may be used, and give good collimated light beams of small diameter without additional correction optics.

Semiconductor diode lasers may be used in various forms, either with direct light production, or utilising "pumping" techniques to produce higher harmonics, which with suitable filtering would allow coverage of the visible spectrum (450 nm–800 nm). Delivery of the laser energy may be directly from gas lasers, from semiconductor diodes through beam shaping optics to compensate for the natural astigmatism of the laser diodes, or though fibre optic delivery systems incorporating collimating optics, which would allow the laser diodes to be positioned away from the scanning head if desired.

Ophthalmic consultants are used to assessing general retinal dysfunctions through the use of colour, and the intention of this new retinal scanning laser ophthalmoscope is to produce an instrument which requires little specialist training for use in image analysis.

It is proposed that this ophthalmoscope utilizes semiconductor diode laser devices for incident beam scanning. An advantage of semiconductor diode lasers is their capability of very fast modulation of the output beam, and this high rate of modulation of the output beam gives this design a further advantage over prior art. Known inventions require that the raster produced by this scanning beam be separately modulated by a beam deflector or modulator since gas lasers cannot be modulated by on/off switching. This separate optomodulator could be a source of beam distortion and so its removal from the device can only be an improvement. The semiconductor diode lasers allow modification of the raster scans to produce patient image targets. Suitable software will allow the position of the image target to be overlaid on the retinal image and so allow easier stabilisation of the eye of the difficult subject. Small children may be attracted by the use of simple cartoon images.

A fundamental component of the proposed design is an ellipsoidal mirror. Existing ophthalmoscopes incorporating mirrors specify that said mirrors be spherical whilst acknowledging the aberrations inherent in spherical mirrors when so utilised. Said mirrors in this context are referred to as retro-scanning mirrors.

A method considered when improving the field of view of scanning laser ophthalmoscopes is to do so by increasing the size of the retro-scanning mirror.

Here, the scanning mirror is chosen specifically to be aspheric in order to optimise the optical path length and to ensure that the scanning mirror allows compensation of the scanned beam across its surface, in accordance with the compensation required to accommodate the natural astigmatism of the eye at the wider angles of view.

The ellipsoidal mirror has two focal points. The incident beam scan is introduced to the mirror through one focus, and the mirror uses the second focus point for directing the scanned illumination beam within the eye, thus allowing the retina to be covered by the scanning beam in two dimensions. However, since the eye is approximately spherical and the pupillary point (or focus point) of the aspheric mirror is located within the optical structure of the eye, it is necessary to determine a novel method to compensate for astigmatic beam aberrations during retinal scanning.

The astigmatic correction of any scanning beam in the pupillary point entails a change of optical power along differential axes as the scan progresses from the central axis of the eye to the periphery of the retina. Existing scanning laser ophthalmoscopes do not address this problem. Currently, the maximum field of view available is about 38° as seen from the pupillary point.

In order to view the retinal periphery with existing laser scanning ophthalmoscopes, it is required that the scan axis of the mirror is rotated relative to the central axis of the eye. The disadvantage of this is that as the scan axis rotation increases a proportion of the image field of the instrument defocuses due to astigmatism and/or defocus and the image produced becomes less informative. Additionally, the instrument presents only the scan data of the image view set by the instrument at any one time, and no means exist to store views and present a composite image with this system.

Thus, the next step is to introduce mechanisms to adjust the focus during scanning in order to obtain wide field digital data with "one pass" scanning. This could be termed an active compensation mechanism and has to compensate for astigmatism and focus change at all points of the scanned image. The idea is to use a focusing telescope, driven by piezo-electric elements, to compensate for these image variations. The piezo electric elements, operating at a sufficiently high speed to allow such execution within the scan cycle, will optimise the image by electronic closed loop feedback from the image data detection and associated electronics.

When a rotating polygon mirror system is used for beam scanning, the scan point traverses-laterally across the facets of the mirror as it rotates. This scan point movement, caused by the fact that the centre of rotation is not a point at the centre of rotation of the front face of the mirror, causes loss of data on the return beam.

The returned data beam has diameter 5–10 times that of the incident beam. Unless compensated for, this can lead to loss of about 80% of the returned beam due to a combination of the fact that the returned beam may overfill the polygon scan mirrors and that this will allow data to be lost as the edges of the mirror facets traverse the beam.

Use of ellipsoidal mirrors (either front surface or Mangin mirrors) in ophthalmoscopes introduce errors. These errors are most notably tangential and sagittal errors namely astigmatism. If the ellipsoidal mirror is so orientated that its sagittal focal point is in front of its tangential focal point this means that its sagittal focus is shorter than its tangential focus. An eye produces its off axis astigmatism from a combination of tangential and sagittal focus errors, in its case the tangential focus being shorter than the sagittal focus. Thus these errors used in opposition can produce a reduced overall astigmatism in an imaging system.

However, since the astigmatism correcting factors will tend to vary at different points of the retinal scan cycle, it is necessary to employ an active closed loop control system which will continuously strive to optimise the detected data signal of the return beam.

The astigmatic compensation mechanism will consist of an assembly of very short focal length optics installed in the incident optical pathway before the scanning of the incident beam. This beam shaping lens assembly will act to focus the incident beam to optimise the illuminated spot on the retina thus controlling the resolution of the image, by means of computer controlled small relative movements of the piezo driven optics in the assembly. The beam will thus be optimised by computer control of the lens assembly operating at rates of compensation similar to those of the active focusing telescope control. On the reverse path, the same compensations will act on the returned data beams before it is registered by the image data detector. In this direction, the assembly will focus the return beam at the confocal aperture thus determining the contrast of the final image registered.

The image data detectors which are photoelectric will produce pixel points of a retinal image of wide field of view and high resolution. The pixel points will form the data and will be stored in a frame grabber array at the maximum resolution of the scanner 54 and the monitor 56 used for display will not limit the data contained to that providing the image frame. The monitor will be used to 'pan' through the total image in high resolution mode. A further refinement is the use of fractal compression techniques to compress the data and provide a complete image at lower resolution- analogous to the 'zoom' lens.

Once displayed, the data is then stored in arrays, on hard or optical disc, for further processing.

Dynamic Spherical Focusing and Residual Astigmatism Compensation.

In the normal eye, once the focus has been set for the incident and return beams, all scanning laser ophthalmic systems are static focus. This is adequate for the fields of view of the instruments concerned, (up to 32 degrees), but for wider field angles, (up to 120 degrees from the pupillary point), particularly if the retina is distorted by detached retina or retinal holes, this is insufficient especially at the retinal periphery. This raises the question that the optical system of the eye, ie the cornea and in particular the lens, is not the uniform structure indicated by the simplified eyes of Gullstrand et al. The crystalline lens in known to be a gradient index structure, and such has a varying optical power across its structure. This variation in lens structure, particularly in combination with varying non-mydriated (undilated) pupils, (the diameter of which acts as an aperture stop), has a considerable effect on the aberrations produced in the incident and return beams at the extremes of field of view. There exists, therefore, scope for active spherical focus compensation for distorted retinal surfaces, and it is possible that once the refractive nature of the eye of the subject is scanned and optimised, an active (dynamic) compensation of spherical focus errors can be instituted in an algorithm, and used to optimise the patients' retinal image.

The laser scanning ophthalmoscope is proposed to be enclosed in an enclosure arrangement whereby the subject will place the head (therefore the eye) in the position to be scanned. This entails that the consultant is unable to see directly the position of the scanning laser beams within the pupil of the eye of the subject. A patient eye positioning system is therefore proposed using an infra-red area illumination. An infra-red area illuminator 58 is directed through a power isolator and reducer filter 60, and fifth 62 and sixth 64 dichroic beamsplitters to illuminate the front of the eye. The returned image is passed through dichroic filters 64, 62 to a infra-red band pass filter 66 and the image received by a small charge coupled device camera 68, and the image displayed on a small video monitor. The incident beam from the scanner system will be easily viewed and the operator will be able to place the incident beam in the plane of the pupil 52 of the subject.

The "Virtual Point Scanning" system is a special case of the general case, of "Addressable Point Scanning", whereby two scanning prisms are used in an orthogonal manner and the speed of one prism is synchronised or varied with respect to the rotation of the rotating polygon and the other scanning prism is synchronised or varied with respect to the galvanometer mirror. This produces a so-called "addressable scan point" within the plane of the pupil of the subject ie, at the pupillary point. This addressable scan point may be allowed to track within the pupillary plane. Virtual Point Scan is a specialist case where only one scanning prism is used in conjunction with the galvanometer drive, and allows the beam angle scan within the pupillary plane to appear to come from one source, the virtual point.

The pupillary point is an arbitrary point within the lens system of the eye, through which all the scan rays should be made to pass, in order to optimise the wide angle capability of the instrument.

Virtual point scanning seeks to ensure that this is undertaken.

We claim:

1. A scanning laser ophthalmoscope for scanning the retina of the eye comprising:

a laser light source;

a first scanning system;

a second scanning system; and an aspherical mirror;

characterized in that:

said laser light source and said first and said second scanning systems are adapted to combine to provide a two-dimensional laser light scan from an apparent point source;

said aspherical mirror has two foci;

said aspherical mirror is adapted to transfer said two-dimensional laser light scan from said apparent point source into an eye; and said ophthalmoscope is adapted to provide said apparent point source at a first focus of the aspherical mirror and to accommodate an eye at a second focus of the mirror.

2. A scanning ophthalmoscope as claimed in claim 1 wherein said aspherical mirror is an ellipsoidal mirror.

3. A scanning ophthalmoscope as claimed in claim 1 or claim 2 including a scanning compensator, wherein said scanning compensator couples said output from said first to said second scanning system so that said two-dimensional laser light scan appears to originate from a point source.

4. A scanning ophthalmoscope as claimed in claim 3 wherein the scanning compensator is a scanning prism.

5. A scanning ophthalmoscope as claimed in claim 3, wherein the scanning compensator is an arrangement of an off-axis aspherical mirror and a galvanometer or rotating polygon.

6. A method of scanning a retina of an eye characterized in that it comprises the steps of providing a two-dimensional laser light scan from an apparent point source at a first focus of an aspheric mirror, placing the pupil of the eye at a second focus of said aspherical mirror, and transferring said two-dimensional laser light scan from said apparent point source to a point on the pupil of the eye via said aspherical mirror.

* * * * *

UNITED STATES PATENT AND TRADE MARK OFFICE
CERTIFICATE OF CORRECTION

PATENT NO. : 5,815,242
DATED : September 29, 1998
INVENTOR(S) : Anderson et al.

It is certified that error appears in the above-identified patent and that said Letters Patent is hereby corrected as shown below:

Cover Page:

[54] WIDE FIELD SCANNING LASER OPHTHALMOSCOPE

Column 1, Lines 1 and 2

WIDE FIELD SCANNING LASER
OPHTHALMOSCOPE

Signed and Sealed this

Twelfth Day of January, 1999

Attest:

*Attesting Officer*   *Acting Commissioner of Patents and Trademarks*